United States Patent
Feldman

(10) Patent No.: US 10,092,409 B2
(45) Date of Patent: Oct. 9, 2018

(54) SUBTALAR ARTHROEREISIS IMPLANT APPARATUS AND TREATMENT METHOD

(76) Inventor: Kent A. Feldman, San Diego, CA (US)

( * ) Notice: Subject to any disclaimer, the term of this patent is extended or adjusted under 35 U.S.C. 154(b) by 0 days.

(21) Appl. No.: 13/034,672

(22) Filed: Feb. 24, 2011

(65) Prior Publication Data

US 2011/0208317 A1 Aug. 25, 2011

Related U.S. Application Data

(60) Provisional application No. 61/307,723, filed on Feb. 24, 2010.

(51) Int. Cl.
*A61F 2/42* (2006.01)
*A61F 2/30* (2006.01)

(52) U.S. Cl.
CPC .... *A61F 2/4202* (2013.01); *A61F 2002/3071* (2013.01); *A61F 2002/3095* (2013.01); *A61F 2002/30579* (2013.01); *A61F 2002/30948* (2013.01); *A61F 2002/30952* (2013.01); *A61F 2002/4223* (2013.01)

(58) Field of Classification Search
CPC ............................................. A61F 2002/4223
USPC ...................................................... 623/21.18
See application file for complete search history.

(56) References Cited

U.S. PATENT DOCUMENTS

| | | | | |
|---|---|---|---|---|
| 5,300,120 A | * | 4/1994 | Knapp ................. | A01K 11/006 623/11.11 |
| 7,033,398 B2 | * | 4/2006 | Graham ................... | 623/21.18 |
| 2005/0010300 A1 | * | 1/2005 | Disilvestro .............. | A61F 2/32 623/18.12 |
| 2005/0197711 A1 | * | 9/2005 | Cachia ...................... | 623/21.11 |
| 2005/0229433 A1 | * | 10/2005 | Cachia ................. | A61B 17/562 36/44 |
| 2006/0041315 A1 | * | 2/2006 | Katz .................... | A61B 17/562 623/21.11 |
| 2006/0190088 A1 | * | 8/2006 | Parks ................... | A61B 17/562 623/21.11 |
| 2006/0245539 A1 | * | 11/2006 | Sukovic ................. | A61B 6/032 378/20 |
| 2007/0198022 A1 | * | 8/2007 | Lang .................... | A61B 17/154 606/88 |
| 2008/0208349 A1 | * | 8/2008 | Graser ................. | A61B 17/562 623/21.18 |

* cited by examiner

*Primary Examiner* — Thomas J Sweet
*Assistant Examiner* — Megan Wolf
(74) *Attorney, Agent, or Firm* — Donn K. Harms

(57) ABSTRACT

A device and method of manufacturing and implanting a custom subtalar arthroereisis implant having side surfaces which are mirrored in topography with the sinus tarsi of a patient. The implant is formed using images of the patient standing in a weight bearing position with their sinus tarsi and the surrounding bone structure in an anatomically correct alignment. Once implanted, the implant urges and maintains the anatomically correct alignment thereby minimizing any patient tendency for abnormal motion between said patent's talus and calcaneus.

8 Claims, 4 Drawing Sheets

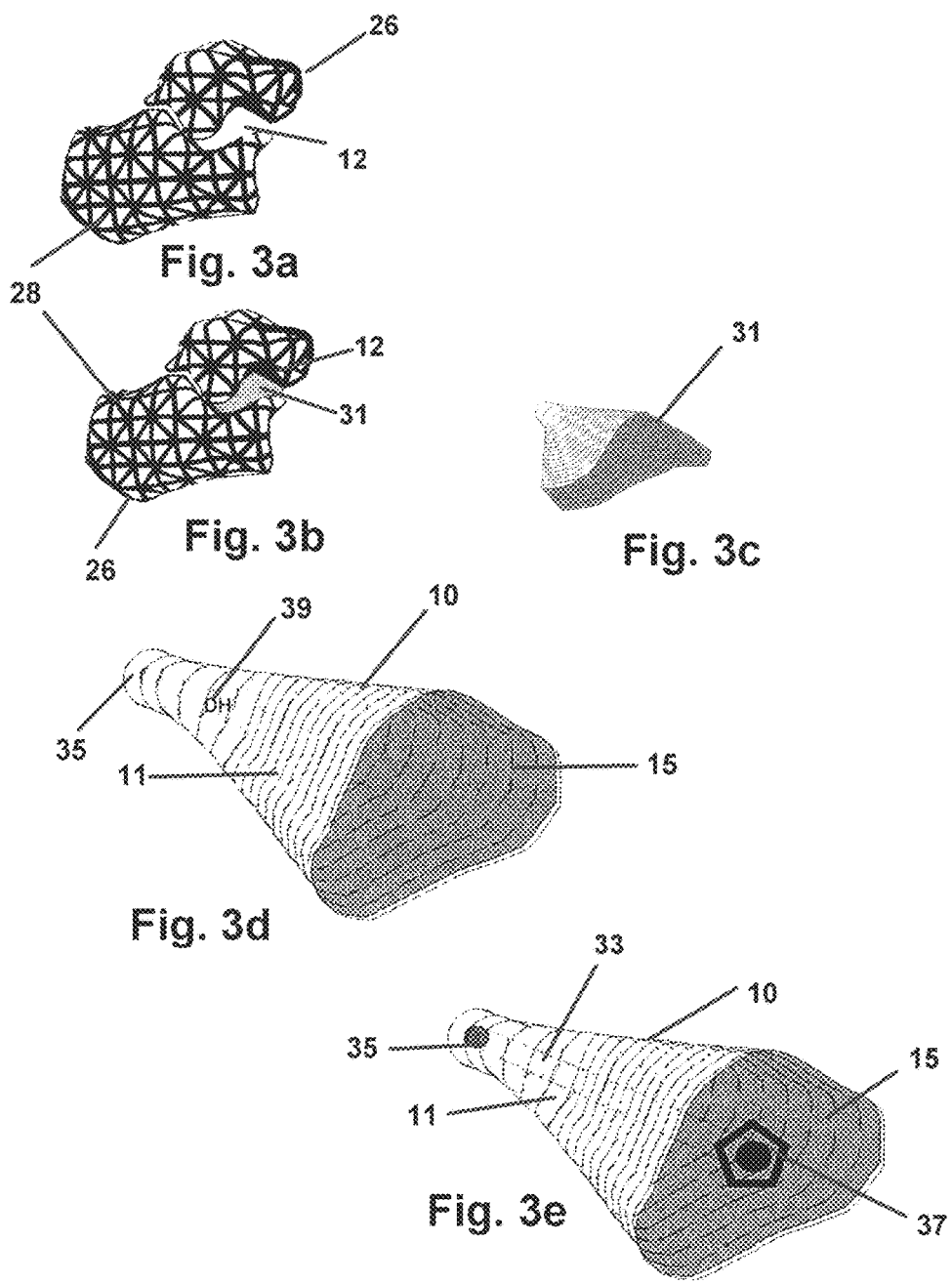

SUBTALAR ARTHROEREISIS IMPLANT APPARATUS AND TREATMENT METHOD

This application claims priority to U.S. Provisional Application 61/307,723, filed on Feb. 24, 2010, and incorporated herein in its entirety by reference hereto.

FIELD OF THE INVENTION

The disclosed device and method relate to the treatment of excessively pronated feet, more commonly known as flat feet. More particularly the device and method herein, relates to the patient-individualized design and manufacture of a surgical subtalar arthroereisis implant configured for treatment of patients with excessively pronated feet. The implant is designed and thereafter formed based upon electronic imaging of a patient's foot while weight-bearing. Digital image files are thereafter employed to form a virtual computer-assisted three dimensional design and subsequent construction of an implant configured for the specific anatomy of each individual patient.

BACKGROUND OF THE INVENTION

In human anatomy, the subtalar joint, also known as the talocalcaneal joint, provides for the articulation between the talus (ankle bone) and the calcaneus (heel bone). A malalignment of the subtalar joint with the bones being provided with this articulation, is a major causative factor or exacerbating factor in many foot pathologies.

Flexible flatfoot is a common such foot disorder caused by hyperpronation and a resulting flattening of the longitudinal arch of the foot in conjunction with excessive calcaneal eversion and forefoot abduction. When the foot is excessively pronated, the talar head rotates medially on the calcaneus and the lateral process of the talus rotates forward.

In general terms, such an excessive pronation may be congenital, or it may occur later in life due to posterior tibial tendon pathologies. Posterior tibial tendon pathologies may be caused by trauma, overuse, inflammatory disorders, and other reasons or combinations of such, or a progressive deformity originating with a congenitally pronated foot.

In addition to causing flat feet, excessively pronated feet contribute to a wide variety of foot ailments including but not limited to: tendinitis, plantar fasciitis, bunions, hammertoes, hallux limitus, and generalized foot pain. Symptoms frequently include pain, weakness, fatigue, and throbbing or cramping discomfort. In children, the resulting symptoms may also include refusal to participate in athletics or refusing or refraining from walking long distances.

Conventional non-invasive treatments, which attempt to provide a means for maintaining proper bone and foot alignment, include foot orthotics, ankle braces, and shoe modifications adapted to properly position and support the foot when bearing weight. Such devices and modifications can be very expensive, especially in younger patients who frequently outgrow them and require replacements.

Arthroereisis is conventionally defined as an operative procedure limiting motion in an abnormally or over-mobile joint. In a flat-footed, hyperpronated patient, a subtalar arthroereisis is employed to engage and restrict the motion between the talus and calcaneus bones. Conventionally, this restriction of motion therebetween is accomplished by placing a mechanically engaged surgical implant within the sinus tarsi, a space, between the talus and calcaneus.

A number of devices are conventionally available for sinus tarsi implantation. These conventional implants are designed and structurally configured to mechanically engage with adjacent bone surfaces and once mounted they restrict subtalar joint motion. The implants purport to improve the alignment of the foot of the patient, and thereby provide an assist in the reduction of foot and ankle pain and pathology.

However, most such devices are of a one-design-fits-all configuration and leave a vast majority of the size, shape, and engagement position to what can best be described as the surgeon or medical professional's experienced estimate. With size, engagement method, positioning, angling, and a host of other factors to consider, there is considerable room for error.

Further, because these threaded or screwed or similar elongated implants employ a permanent mechanical engagement with the bones involved, at a very small space on the circumference of the implant, there is an immense amount of force imparted to each respectively engaged bone on the very small surface area of engagement with the implant.

This small area of engagement, and due to a mismatch in the chosen implant shape, and the sinus tarsi anatomy, there are abnormal impact stresses applied to the bones. Such stress is a common cause in treated patients of post-arthroereisis pain which is generally one of the major factors patient's choose such implants in the first place. While this mechanical engagement and one-design-fits-all concept works well in mechanical components, in the human body, employing a hard metallic member of a singular shape or configuration, and implanting it through mechanical engagement in a biologically diverse population of patients all having infinitely variable bone and joint positioning aspects, is less than ideal.

For example, U.S. Pat. No. 7,033,398, (Graham) teaches the employment of a generally cylindrical implant having two sections including a frustum of a right cone portion as well as an integral extension. The frustum or coned portion is operably positioned within the lateral or sinus region of the sinus tarsi and a smaller diameter cylindrical portion of the implant is engaged on the medial side of the implant and is operably engaged within the canalis tarsi.

The surface of the disclosed implant contains channels or threads or a roughened texture in selected engagement regions. These engagement regions mechanically engage with the contacting bones in small surface areas to achieve a mechanical engagement with the bones being stabilized.

As taught, the Graham reference, included herein by this reference, is an exemplar of the current state of the art in this type of implant where cylindrical elongated implants, are mechanically engaged with adjacent bones, at very small surface area contact points, to maintain a certain positioning. As noted, choosing the right size, and shaped implant, and contact engagement surfaces, and angle of engagement, amongst other variable factors, is up to the medical professional as is positioning. Further, when deciding at what position to position the foot bones of the patient, to employ the implant to hold that position, it is again a professional educated guess, since the implant does not determine the ultimate position of the engaged bones. Instead, the foot is held where the medical professional believes is the proper weight-bearing position, and then the insert is engaged mechanically. This engagement holds the contacted bones in a position relative to each other to provide a means to maintain the limited motion for the patient to be able to acquire that proper position when healed. Consequently, the medical professional must use x rays and professional estimates of what is needed and how it should be engaged which can be less than accurate and fail to product optimum patient outcomes.

As such, there exists an unmet need for an implant adapted for positioning in the sinus tarsi, which is custom-configurable to correct an excessive talar displacement and calcaneal eversion in each respective individual patient. Such a device should be inert when positioned in the body. Further, such a device should be modeled, and thereafter formed, from the actual images of bone configurations of each respective patient, while their foot is weight-bearing at the proper angle, to thereby yield an implant having an exterior surface configuration which is adapted to match the weight-bearing bones and contact surfaces each patient individually, at the largest possible contact surface areas. Such an implant should thereby yield maximum comfort concurrently with maximized results and improvement to the bio mechanics of the foot during weight bearing since once inserted, the surfaces of the implant will cause the contacted bone surfaces, to maintain the weight-bearing position ascertained in the 3D imaging as proper.

In this respect, before explaining at least one embodiment of the implant invention and method herein in detail, it is to be understood that the invention is not limited in its application to the details of construction and to the arrangement of the components set forth in the following description or illustrated in the drawings nor the steps outlined in the specification. The disclosed sinus tarsi area implant is capable of other embodiments and of being practiced and carried out in various ways as those skilled in the art will readily ascertain once educated in the novel device and method of this application.

Also, it is to be understood that the phraseology and terminology employed herein are for the purpose of description and should not be regarded as limiting in any manner. As such, those skilled in the art will appreciate that the conception upon which this disclosure is based may readily be utilized as a basis for designing other methods and systems for carrying out the several purposes of the sinus tarsi implantation device disclosed herein. It is important, therefore, that the claims be regarded as including such equivalent construction insofar as they do not depart from the spirit and scope of the present invention.

OBJECTS OF THE INVENTION

An object of this invention is the provision of a highly customized implant, dimensioned using three-dimensional imagery of the weight bearing patient, for positioning in the sinus tarsi.

An additional object of this invention is the provision of such a prosthesis which is surface-customized, using a three-dimensional weight-bearing image of the patient, and means to form an exterior surface of the implant, which in three dimensions substantially mirrors and/or mates with the individual patient's anatomical area of the sinus tarsi while weight-bearing, thereby providing a substantially perfect fit therein, and allowing the implant to determine the proper positioning of the bones of the patient.

An additional object of this invention is the provision of such three-dimensional implants which may be formed using any means for forming an implant from a three-dimensional image such as a lathe, a mold, or a three-dimensional printer, or future devices adapted to receive three-dimensional virtual images and creating a model thereof.

Yet another object of this invention, is the provision of an implant which will substantially remove the guess work of the medical professional in the operating room, as to the proper final positioning of the patient's bones relative to each other, to secure them in the proper position for weight bearing.

These together with other objects and advantages implant and customization method which will become subsequently apparent to those skilled in the art, reside in the details of the construction and method herein as more fully hereinafter described and claimed, reference being had to the accompanying drawings forming a part thereof, wherein like numerals refer to like parts throughout.

SUMMARY OF THE INVENTION

The device and method disclosed herein allow for the provision to each individual patient, a highly customizable implant based on the three-dimensional areas while weight bearing with their foot held in the proper position. Employing a means for formation of a three dimensional image such as a CAT Scanner or MRI device, providing data to appropriate software, the resulting implant is customized to the anatomical dimensions and bone engagement of each individual patient. To that end the resulting implant is given an exterior surface which topographically on all sides is configured with surfacing facets and features anatomically mated to the weight-bearing patient's adjacent foot structures within the area of the sinus tarsi.

The implant shape and topography on all surfaces is determined in a manner that is customized to each patient by employing three-dimensional shape data from one or a combination of electronic imaging modality devices such as an MRI (magnetic resonance imaging), a CT (computed tomography), a CBCT (cone beam computed tomography), ultrasound, active triangulation, passive triangulation and confocal scanning. Of course, any such device which will yield the three-dimensional coordinate data to software adapted to the task of ascertaining the volume, exterior shape, and topographical surfaces of the implant, in a fashion to customize it for a fitment in the area of the sinus tarsi of each individual patient is anticipated as being included herein.

Currently, a horizontally disposed CAT scanner is employed, to capture a three-dimensional image of a patient's foot, after the foot has been placed in the proper posture, and while the patient bears weight on the foot. The employment of 3D imaging to capture the dimensional characteristics of the bones of the patient's properly positioned weight bearing foot, thereby yields an implant adapted to engage and hold the foot in the proper position.

Using the resulting three-dimensional rendering of electronic coordinates, 3D modeling software is then employed to calculate and ascertain the exact shape and topography of each surface area for each implant in a fashion customized for each respective patient in a matter to maximize, success, comfort and performance.

In use, the method herein employs the following steps:

I) employing a three-dimensional imaging means to digitize a patient's weight bearing three-dimensional anatomic shape of the sinus tarsi of a patient. The patient's foot may be either placed in a proper position and held there during weight bearing in on mode, or the software may be employed to align the bones of the foot to proper posture and thereby render the weight-bearing 3D digitized image. The imaging may employ multiple images depending on a variety of foot positions; weight bearing positions, semi weight bearing positions, non-weight bearing positions, neutral positions, or a variety of less than maximally pronated positions;

ii) The three-dimensional coordinates yielded by the electronic imaging are in a second step employed to yield a virtual model of the respective patient's sinus tarsi as a data record or image, in the form of a negative space;

iii) The data record so recorded is converted from the negative space image of the sinus tarsi, into a positive shape form having an multi faceted exterior surface;

iv) Employing software adapted to the task, and professional judgement if needed, a digital editing the sinus tarsi positive form is then performed and final topographical surfaces and dimensional configurations are ascertained in a final dimensional configuration for the individual patient;

v) based on this final dimensional configuration, the arthroereisis implant is formed, employing a means for implant formation adapted to employ the three dimensional final dimensional configuration data that have been obtained by the scan and if applicable, optimized;

vi) once the implant is formed, a variety of textures may be imparted to the exterior terrestrial surface areas of the implant, these surface textures are adapted for one or a combination of promoting soft tissue ingrowth into the implant, or to provide resistance to implant motion once implanted within the patients sinus tarsi;

vii) optionally, slots may be formed into the exterior surface a distance into the body of the implant to allow for a surface flex and thereby provide a means to facilitate shock absorption during movement while the patient's foot is weight bearing.

Taken into consideration, the electronic digital model can be modified to achieve the desired goal of subtalar joint motion control and distribution of weight bearing force within the implant or across bony surface area.

Formation of the implant itself, its faceted exterior and dimensions and surfacing can be provided by one or a combination of milling, grinding, or rapid prototyping such as three dimensional printers or computer driven mills. Such will facilitate onsite manufacture at a physician's office, a laboratory or a medical implant manufacturing facility.

In one mode of the device and method, the three-dimensional coordinate data captured above, and describing the solid representation of the sinus tarsi, are then converted into an IGES data format. This is performed using, for example, a software such as Solid-Works (Solid-Works Corp., Concord, Mass., USA). This industry standard IGES file thereafter allows generating a CNC sequence to machine adapted for form a subtalar arthroereisis implant from a piece of bio-compatible material such as titanium, titanium alloy, and surgical stainless steel or ceramic material, or bio-compatible plastic or synthetic material such as PEEK, or polyethylene. After removing the excess material if applicable, a manual cleaning, degreasing, polishing, etching, disinfecting/sterilizing and packaging may be performed which will render the implant ready for surgical insertion.

Optionally, in order to facilitate the integration of the implant into soft tissue further treatments, according to prior art, are possible. Sandblasting with ceramic particles for example create a roughened surface to significantly increase surface area. Other suitable coatings can be applied to facilitate soft tissue in-growth/binding include but are not limited to pharmaceuticals, ancestral cells, and proteins.

In another mode of production of the implant from the final three-dimensional data, a three-dimensional printer is employed which is engaged to a supply of the appropriate polymer to form the implant. Thereafter, the implant is formed using layers of material placed by multiple passes of the printing head of the 3D printer.

With respect to the above description then, it is to be realized that the optimum dimensional relationships for the parts of the invention, to include variations in size, materials, shape, form, function and manner of operation, manner of formation, assembly and use, are deemed readily apparent and obvious to one skilled in the art, and all equivalent relationships to those illustrated in the drawings and described in the specification are intended to be encompassed by the present invention. Therefore, the foregoing summary and following description are considered as illustrative only of the principles of the invention to form a customized implant. Further, since numerous modifications and changes will readily occur to those skilled in the art, it is not desired to limit the invention to the exact construction and operation and steps of formation shown and described, and accordingly, all suitable modifications and equivalents may be resorted to, falling within the scope of the invention.

BRIEF DESCRIPTION OF THE DRAWINGS

FIG. 3a shows the result of the processing of the images of 2C by software running on a computer adapted to produce and render 3D images.

FIG. 3b depicts the second step wherein the void of the sinus tarsi is determined and its 3D topography and its shape and contours.

FIG. 3c depicts a rendering of a positive 3D image of the void determined in FIG. 3b, mirroring the topography thereof.

FIG. 3d depicts the implant formed from the 3D image of FIG. 3c using a prototyping device adapted to employ 3D imaging to produce the implant having contoured exterior surfaces and a topography substantially mirroring that of the void of FIG. 3a.

FIG. 3e depicts the implant of FIG. 3d also having an axial guide member running therethrough, the distal end of which provides a means for securement of the implant in the patient.

FIG. 4a depicts the exterior surface of the implant having recesses formed therein to increase frictional engagement with the surface of the sinus tarsi and to provide a means for shock absorption during movement by deflection of material into the recesses.

FIG. 4b depicts a textured surface for the implant having the same functional characteristics as that of the ridges of FIG. 4a.

DETAILED DESCRIPTION OF THE INVENTION

Figure 1:
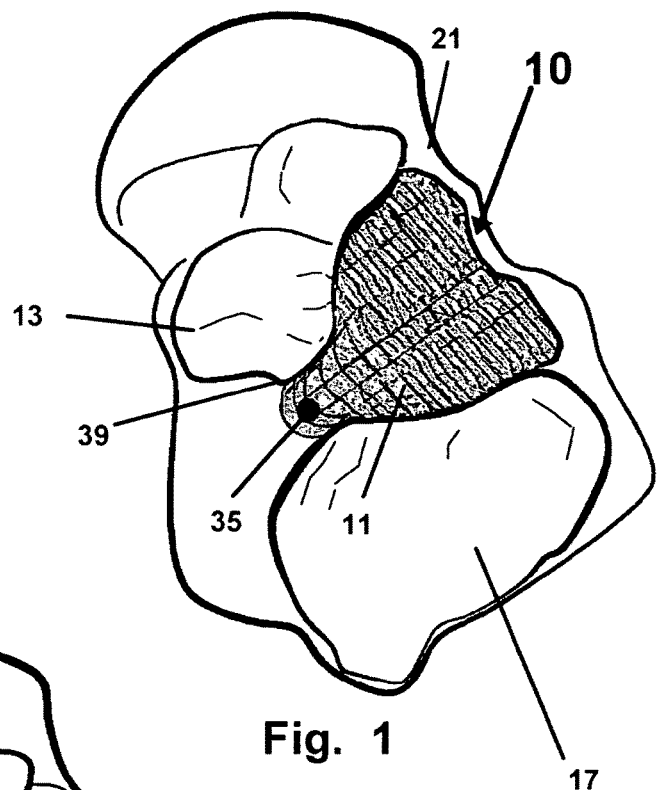
FIG. 1 is a horizontal sliced view through the anatomic space of the sinus tarsi and depicts the disclosed implant device, formed by the method herein, engaged therein in a maximum contact with the surfaces of surrounding bone structures.

Referring now to the drawings 1-4, where similar components and structures are denoted with like numerals, there is seen in FIG. 1 an illustration of the device 10 herein formed by the disclosed method for the device 10. As depicted in the horizontal sliced view through the anatomic space of the sinus tarsi 12, the device 10 is engaged therein and has been formed with the proper topography and resulting sides and surfacing to maximize contact of the device 10 surfaces 11 with the adjacent bone structures of the middle calcaneal facet 13 and the shown posterior facet 17. The surfaces 11 so formed, yield a device whose dimensions and exterior surfaces 11 which substantially mirror the topography of the surrounding anatomic space of the sinus tarsi 12.

So implanted, the device 10 provides a means to substantially maintain the relative positions of the bones engaged with the sides 11 of the device, to maintain the patient's foot in a substantially proper posture or position for a proper and healthy weight-bearing stance as originally determined and imaged in multiple images and formed to a 3D image using software adapted to the task.

As can be seen, the surfaces 11 of the exterior of the device 10, are formed using 3D imaging, and means of manufacture to form the body of the device 10 to have surfaces 11 sized and positioned, to match the imaged surfaces of the surrounding anatomic space, using the plurality of digital images taken when the patient is actually standing in the proper weight-bearing posture. Consequently, the device 10, once implanted provides a means to urge and thereafter maintain the contacted surrounding bones to their proper positioning relative to the other bone structures. This provides a much more predictable and positive outcome for the patient than the current art shown in FIG. 2, where the one or a plurality of medical professionals make an educated guess as to the proper positioning, and employ a mechanically engaged member 19 to engage with small surface areas on adjacent bones, to hold them in position. The optimum outcome of the surgery using the disclosed device 10 and method is highly likely due to the elimination of many of the variables noted earlier, which continue as a problem with prior art.

Figure 2:
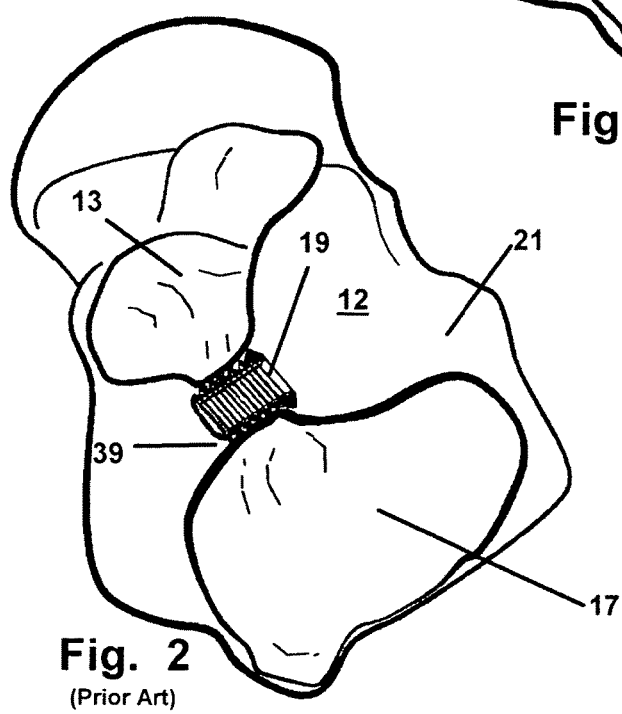
FIG. 2 is a second horizontal sliced view through the anatomic space of the sinus tarsi depicting prior art typical of many conventional implants which employ mechanical members with mechanical engaging surfaces such as threads, to engage with bone surfaces at small contact points.

As shown in FIG. 2, engaging an elongated member 19 by screwing or otherwise mechanically engaging it with small surface areas on adjacent bones, places a major force on the engagement points when the patient is standing and bearing weight. This has in the past resulted in a chronic pain to many patients. Additionally, as noted, the current art has multiple assumptions and professional judgement estimates which must all accurately meld together, to actually provide the support to the patient which will allow them to stand naturally when weight bearing.

The body 15 portion of the implant device 10 herein is formed of medical grade polymer, plastic, rubber, or metal, or combinations of one or more thereof, or other materials which may be formed to substantially mirror the topography of the anatomic space of the sinus tarsi 12, using a 3D image file, assembled by software from multiple images of the patient taken while weight bearing and with their foot in the desired posture-correct position. It is anticipated the device 10 may be formed of one or a combination of a group of materials consisting of polymers, stainless steel, titanium, titanium alloy, cement, zirconium oxide, ceramics, synthetics, elastics, and plastics, depending on the patient.

Figure 2A:
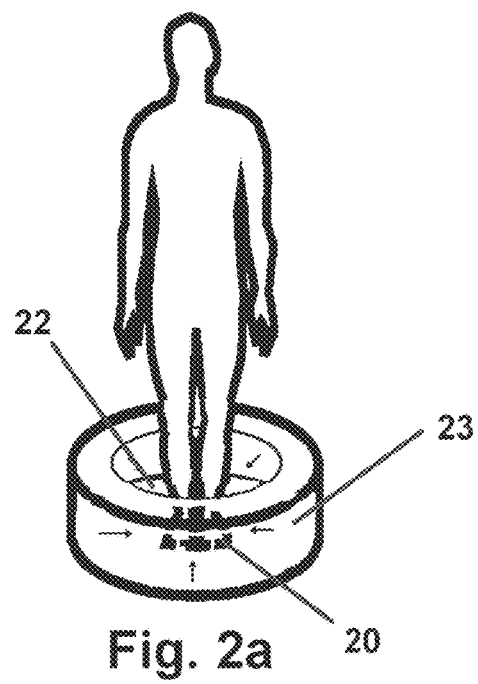
FIG. 2a depicts the first step of the method herein wherein a plurality of electronic images of the patient are taken while the patient is in the proper ankle posture and weight bearing.
Figure 2B:
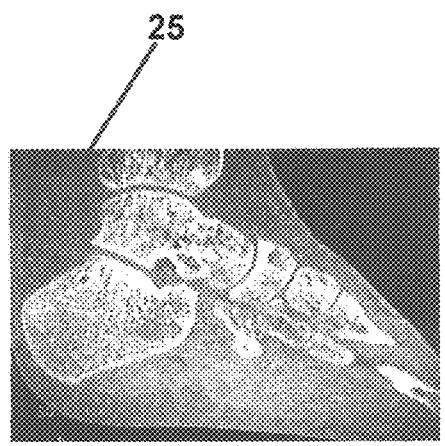
FIG. 2b depicts an electronic or digital image of a slice through the weight bearing foot of the patient.

Seen in FIG. 2a is the initial step in obtaining digital imaging of the patient's foot, wherein the patient's foot is positioned in the proper anatomical position 20, within the image capturing area 22 of an electronic imaging device 23, such as a CT scanner, a CBCT device, or an MRI imaging device, or other such digital imaging devices. The imaging device 23 is preferably situated to allow a plurality of weight bearing images 25 to be taken while the patient's foot is also in the desired posture-correct position.

It should be noted that with the advance of software and biomechanics, in the future it may be possible to image the patient's foot and ankle in a not weight-bearing position, and thereafter employ software to move actual images of their bones in a biomechanical function. Thus, the final 3D image of the patient in the proper posture-correct position to cure or treat their flat feet, may be renderable using software having the biomechanical ability to move the still images of the patient. Such is anticipated if it yields a final image of the patient in a proper weight bearing position to yield a posture correct outcome with the implant device 10.

Currently, with the patient standing in a posture-correct weight bearing position, a CT scanning device is employed for the imaging device 23 which is adapted to make sliced images 25, at varying angles, of the weight bearing foot of the patient, sufficient to be assembled into a 3D image 26 such as the wireframe images in FIGS. 3a and 3b.

It is most important, and therefor highly preferred, to have the patient's foot the noted weight bearing position during the entire imaging process, and to have their foot positioned in the proper anatomical or posture-correct position by the physician. If required the foot and ankle should be held in position by a brace.

This positioning places all of the bones surrounding the anatomic space of the sinus tarsi 12, to their proper angle and positioning relative to each other, such that the implant device 10 will be formed to fit within the anatomic space of the sinus tarsi 12, and maximize contact with the surrounding bone surfaces. When finally implanted, the device 10 will provide a means to urge the surrounding bones to the proper position and provides a means to maintain said sinus tarsi in an anatomically correct alignment and a means for minimization of the patient's tendency for abnormal motion between said patent's talus 21 and calcaneus thereby maintaining the bone structure of said patient surrounding said sinus tarsi, in said anatomically correct alignment. The possibility of pain from the implant such as is experienced by the prior art is minimized since the implant maintains the surrounding bones in their proper by employment of maximum surface contact between the sides of device 10 and walls forming the sinus tarsi 12 cavity.

As can be surmised, the disclosed device and method yield a much more successful patient outcome as opposed to the small points of contact with mechanically engaged devices and inserts noted in the prior art and depicted in an example in FIG. 2. This maximizing of contact provides a means to widely distribute the forces imparted to the bone structure by an adult standing on their feet.

In the imaging processes, the anatomic space of the sinus tarsi 12 is electronically imaged from a plurality of angles using the means for digital imaging, with the patient as noted, in a weight-bearing position as in FIG. 2a. This plurality of images 27 is produced in an electronic or digital format such as a Digital Imaging and Communications in Medicine (DICOM) format, as a means to provide detailed images 25 to be assembled to form a detailed topographically-correct three dimensional electronic image 14 of a patient's sinus tarsi 12.

Figure 2C:
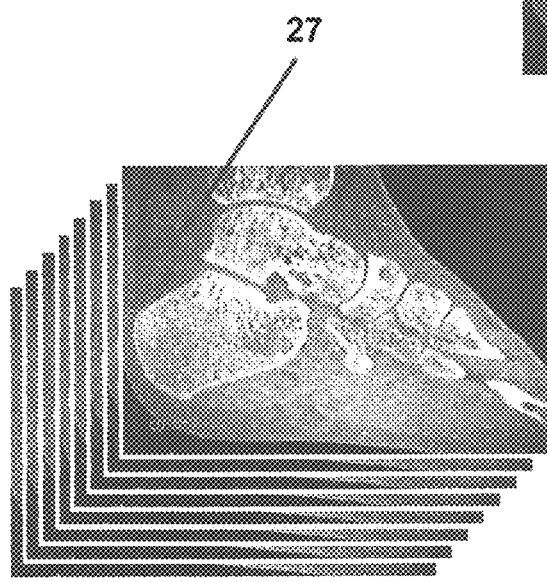
FIG. 2c depicts the plurality of images taken from different angles which are provided to software running on a computer adapted to form a three dimensional image from such a plurality.
Figures 4A, 4B:
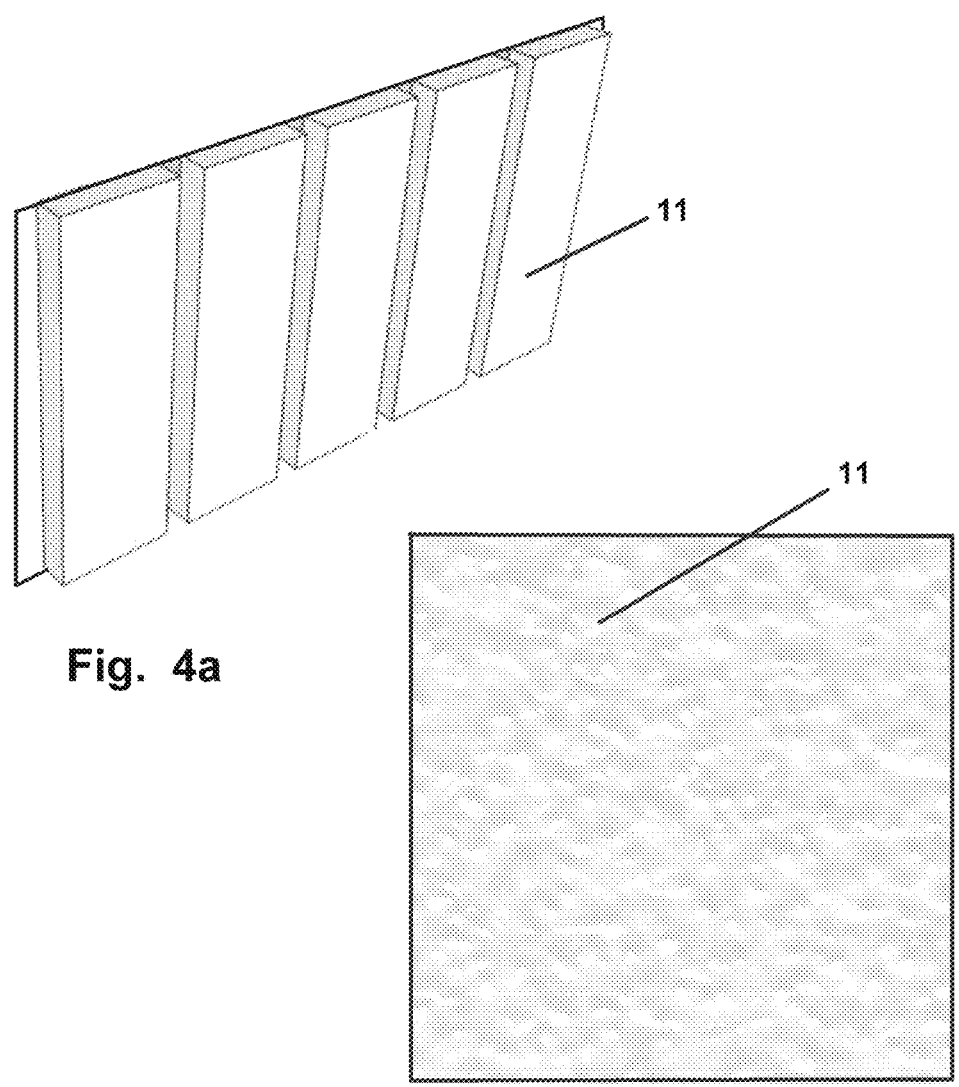

Employing this plurality of electronic digital images 27 as seen in FIG. 2c, software and computers adapted to the task, assemble a digitized three-dimensional image such as the wireframe 28 (FIGS. 3*a* and 3*b*) rendering of bone surfaces surrounding, and defining the anatomic shape 31 of the anatomic space of the sinus tarsi 12.

As noted, the size, shape, and topographical surfaces of the void are determined by employing software and an electronic means for production of three-dimensional digital images 28 to determine a mirrored configuration for an implant device 10, as shown in FIGS. 3*b* and 3*c*, using the 3D digital image file and software adapted to the task. Those skilled in the art will realize that many software and computer programs are capable of assembling 3D image files from multiple images 27, and any current or future such software and computer hardware that is capable of this process is considered within the scope of this invention.

Currently the 3D file employed for rapid prototyping or other means for formation of the device 10 customized to a patient employs the following steps although as noted, other software and hardware will do the same and therefor this explanation should in no fashion be considered limiting.

1) Acquisition of two dimensional DICOM images 25 of the foot and/or ankle via CT, CBCT, or MRI while the patient is in a weight-bearing, posture-correct position.

2) The DICOM Images of the foot and/or ankle are then imported into Mimics Software Suite Materialise, Brussels, Belgium).

3) Anatomic Segmentation is performed using the Mimics program to select the bone segments.

4) Anatomic Isolation is then performed selecting the talus and calcaneus in the Mimics program.

5) From an image of the sinus tarsi, the anatomic space (FIG. 1) a Mimics program design void, is converted into a positive 3D design image, using the Mimics software.

6) The positive design image of the sinus tarsi and tarsal canal is cropped using the Mimics software tool suite thereby creating a rough draft custom subtalar arthroereisis implant device.

7) The rough implant design is then modified using Mimics software tools to smooth out pits and rough edges (defeaturing) along with other modifications as needed using Mimics to edit the implant surface mesh.

8) The Materialise Mimics Software Suite 3-Matics module program is then used to modify the rough implant by adding the various components thereto including a cannulation guide tunnel, inserter, anchoring point, surface texturing to maximize frictional engagement and/or tissue grown, a tarsal canal anchor and patient identifier upon the device.

9) The Mimics STL+module then prepares the custom designed implant file such as an IGES data image file, for export to a rapid prototyping system for manufacture.

Of course other presently available and future offered 3D software and hardware adapted to the above task, may be employed and such is anticipated within the scope of this application and claims.

Thereafter the implant device 10 is formed as a subtalar arthroereisis implant, as in FIG. 3*c*, using a prototyping or manufacturing means to convert the electronic data image file mechanically into to a three dimensional implant (3*d*).

In addition to the medical grade polymer or metal or other material forming the exterior surfaces 11 of the implant device 10, during formation surface texturing 33, a tarsal canal anchor point 35, an insertion member 37, and patient identifier 39 may be included upon the implant device 10.

The anchor point 35 formed on the distal end of the implant device 10 would provide for initial and ongoing anchoring of the device to hold it properly within the patient. Means of anchoring at this anchor point 35 may be forming the exterior surfaces 11 of the implant device 10 to yield a circumference of the anchor point 35, slightly larger than the circumference of the tarsal canal 39, and forming the surface 11 from a compressible material which will rebound to provide a biased frictional engagement. Alternatively, there can be a mechanical operation coaxial along the insertion member 37 to cause an expansion of the circumference of the anchor point 35. Medical grade adhesive may also be employable in some cases.

Anticipated prototyping devices employable presently include a three-dimensional printer, a CNC machine, a rapid prototype laser lithography or molding device, or other means to form the implant 10 using the coordinates of the 3D digital file. Of course any rapid prototyping or manufacturing device capable of employing the data image file, to produce the implant device 10 optionally inclusive of any one or a combination of components noted above, is anticipated within the scope of this application and claims.

Optionally, as noted, once so formed, or during formation if practical, the exterior surface of the implant device 10 may be adapted with a surface texture 33 or recesses or the like to encourage ingrowth of soft tissue, and to encourage cell growth and/or maximize the frictional engagement and maintain the implant device 10 in position in the patient once implanted.

Using the disclosed method, each patient may have individualized implant device 10 formed using three dimensional electronic images of the anatomic space of their respective sinus tarsi 12. With the fast evolving 3D manufacturing and rapid prototyping devices coming on line now and in the future, the implant devices 10 may be formed on site at the doctors office or hospital, or off site by communication of the electronic three dimensional image file to a facility adapted to form the implant using the image file.

As noted above, while the present invention has been described herein with reference to particular embodiments thereof and steps in the method of production, a latitude of modifications, various changes and substitutions are intended in the foregoing disclosures, it will be appreciated that in some instance some features or steps in formation of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

Further, the purpose of any abstract of this specification is to enable the U.S. Patent and Trademark Office, the public generally, and especially the scientists, engineers, and practitioners in the art who are not familiar with patent or legal terms or phraseology, to determine quickly from a cursory inspection the nature and essence of the technical disclosure of the application. Any such abstract is neither intended to define the invention of the application, which is measured by the claims, nor is it intended to be limiting, as to the scope of the invention in any way.

What is claimed is:

1. A subtalar arthroereisis implant, for correcting anatomical alignment of a patient's ankle bone structure comprising:
    an implant configured for insertion to an implanted position within a void, said void having a shape defined by a topography of all of a plurality of bone surfaces surrounding an entire area of an anatomic space of a sinus tarsi cavity of a foot of a patient while in a weight bearing position;

said implant having a monolithic body, said monolithic body formed of compressible material, said monolithic body having a circumferential exterior surface extending from a first end of said monolithic body to a distal end of said monolithic body;

a plurality of facets formed into said circumferential exterior surface defining a topography of said circumferential exterior surface of said monolithic body of said implant;

said topography defined by said plurality of facets forming said circumferential exterior surface of said monolithic body to a surface topography which is a mirror image of said shape of said void defined by said topography of all of said plurality of bone surfaces surrounding said entire area of said anatomic space; and said monolithic body is positionable to an implanted position with said circumferential exterior surface of said monolithic body anatomically mated in respective contacts of respective said plurality of facets against respective said bone surfaces of all of said plurality of bone surfaces surrounding said entire area of said anatomic space.

2. The subtalar arthroereisis implant of claim 1, additionally comprising:

an anchor portion extending from said distal end of said monolithic body of said implant;

said anchor portion having an exterior surface defining a circumference of said anchor portion sized larger than an interior circumference of bone surfaces defining an area of a tarsal canal communicating with said sinus tarsi cavity; and said exterior surface of said anchor portion forming a biased contact against said bone surfaces defining said area of said tarsal canal, when said implant is in said implanted position.

3. The subtalar arthroereisis implant of claim 2, additionally comprising:

said circumferential exterior surface of said monolithic body having a surface texture thereon, said surface texture enhancing a frictional engagement of said monolithic body against all of said plurality of bone surfaces surrounding said entire area of said anatomic space of said sinus tarsi cavity, said surface texture adapted for cell growth therein.

4. The subtalar arthroereisis implant of claim 3, additionally comprising:

a cross-sectional area of said first end of said monolithic body being larger than a cross-sectional area of said distal end of said monolithic body.

5. The subtalar arthroereisis implant of claim 2, additionally comprising:

a cross-sectional area of said first end of said monolithic body being larger than a cross-sectional area of said distal end of said monolithic body.

6. The subtalar arthroereisis implant of claim 1, additionally comprising:

said circumferential exterior surface of said monolithic body having a surface texture thereon, said surface texture enhancing a frictional engagement of said monolithic body against all of said plurality of bone surfaces surrounding said entire area of said anatomic space of said sinus tarsi cavity, said surface texture adapted for cell growth therein.

7. The subtalar arthroereisis implant of claim 6, additionally comprising:

a cross-sectional area of said first end of said monolithic body being larger than a cross-sectional area of said distal end of said monolithic body.

8. The subtalar arthroereisis implant of claim 1, additionally comprising:

a cross-sectional area of said first end of said monolithic body being larger than a cross-sectional area of said distal end of said monolithic body.

* * * * *